United States Patent [19]

Jeppsson

[11] Patent Number: 5,788,845
[45] Date of Patent: Aug. 4, 1998

[54] QUANTITATION OF CARBOHYDRATE DEFICIENT TRANSFERRIN IN HIGH ALCOHOL CONSUMPTION BY HPLC

[75] Inventor: Jan Olof Jeppsson, Malmo, Sweden

[73] Assignee: Biolin Medical AB, Stockholm, Sweden

[21] Appl. No.: 872,329

[22] Filed: Jun. 10, 1997

Related U.S. Application Data

[63] Continuation of Ser. No. 591,542, filed as PCT/SE94/00684 Jul. 11, 1994, abandoned.

[30] Foreign Application Priority Data

Aug. 6, 1993 [SE] Sweden ............................ 9302573

[51] Int. Cl.$^6$ ............................................. B01D 15/08
[52] U.S. Cl. ........................... 210/635; 210/656; 436/132
[58] Field of Search .............................. 210/635, 656, 210/659, 198.2; 436/132

[56] References Cited

U.S. PATENT DOCUMENTS

| | | | |
|---|---|---|---|
| 4,169,676 | 10/1979 | Kaiser | 436/132 |
| 4,448,767 | 5/1984 | Bryant | 424/85 |
| 4,626,355 | 12/1986 | Joustra | 210/635 |
| 4,814,280 | 3/1989 | Peterson | 436/132 |
| 4,883,752 | 11/1989 | Eda | 435/68 |
| 5,126,271 | 6/1992 | Harasymiw | 436/132 |
| 5,352,616 | 10/1994 | Sundrehagen | 436/501 |
| 5,460,970 | 10/1995 | Truitt | 436/132 |

FOREIGN PATENT DOCUMENTS 8503578  8/1985  WIPO ....................... 210/198.2
9119983  12/1991  WIPO ....................... 210/198.2

OTHER PUBLICATIONS

National Library of Medicine database, Medline, File Med 91, NLM Accession No. 92110905, Stibler H. et al.
National Library of Medicine database, Medline, File Med 85, NLM Accession No. 87251085, Pask–Hughes R.A. et al.
National Library of Medicine database, Medline, File Med 85, NLM Accession No. 88047293, Petren S. et al.
National Library of Medicine database, Medline, File Med. NLM Accession No. 94007163, Jeppsson J.O. et al.
Dialog Information Services, File 155, Medline 66–90/May, Accession No. 03616083 Medline Accession No. 78250083, Hellsing K. et al.
Snyder, Introduction to Modern Liquid Chromatography John Wiley & Sons, New York, 1979, pp. 135–139 amd 542–549.

*Primary Examiner*—Ernest G. Therkorn
*Attorney, Agent, or Firm*—Sixbey Friedman Leedom & Ferguson; Frank P. Presta

[57] ABSTRACT

A method for determining the amount of carbohydrate deficient transferrin (CDT) in blood serum involves saturating a sample of the blood serum with iron to provide isoforms of transferrin, separating the isoforms of transferrin from other serum proteins in the sample, and developing a chromatogram which relates the separated isoforms with different pI values. The separation step is preferably carried out in an ion exchange column using a salt gradient and the chromatogram is preferably developed using a high performance liquid chromatograph (HPLC). The method is particularly useful for identifying heavy alcohol consumption in a person, which is related to isoforms of transferrin having pI values of 5.9 and 5.7.

16 Claims, 4 Drawing Sheets

GRADIENT PROFILE

| t (min) | A % | B % | C % |
|---|---|---|---|
| 0 | 100 | 0 | 0 |
| 3.0 | 100 | 0 | 0 |
| 5.0 | 90 | 10 | 0 |
| 18.0 | 66 | 34 | 0 |
| 18.1 | 0 | 0 | 100 |
| 22.0 | 100 | 0 | 0 |
| 32.0 | 100 | 0 | 0 |

*FIG. 3* ns having pH values
QUANTITATION OF CARBOHYDRATE DEFICIENT TRANSFERRIN IN HIGH ALCOHOL CONSUMPTION BY HPLC This application is a continuation of application Ser. No. 08/591,542 filed Feb. 6, 1995, now abandoned, which, in turn, is a 371 of PCT/SE94/00684, filed Jul. 11, 1994.

FIELD OF THE INVENTION

The present invention relates to a method for separation and quantitation of carbohydrate deficient transferrin (CDT) in order to decide a person's alcohol consumption.

BACKGROUND OF THE INVENTION

Alcohol causes extensive damage to its victims and their families and significant costs for society through its associated morbidity and mortality. Early recognition and treatment have shown to be beneficial for the individual and cost effective for society. Sensitive, specific, rapid and inexpensive methods for identifying the individuals at risk of complications to drinking in different populations are needed. Numerous procedures designed to detect heavy drinkers have been developed during the past thirty years. Conventional laboratory tests such as γ-glutamyltransferase (γ-GT), mean corpuscular volume (MCV), aspartate or alanine aminotransferases (AST or ALT), α-lipoproteins and ferritin have been used for many years as biochemical markers of alcohol abuse, but have low diagnostic sensitivity and specificity. A qualitative change in isoforms of transferrin in cerebrospinal fluid and serum of patients with alcohol related cerebellar tremor has been reported. The isoforms related to alcohol abuse contained less sialic acid than other isoforms and can therefore be distinguished according to charge. Several techniques for separation of isoforms have been introduced but they are generally laborious, non-quantitative and expensive. Chromatofocusing, disposable mini-columns combined with RIA (radioimmunoassay) and electrofocusing followed by immunofixation, Western blotting or zone immunoelectrophoresis are the available techniques. Transferrin, the iron-transporting protein in blood, is a glycoprotein with two bi- or tri-antennary carbohydrate chains, each terminated with two or three sialic acids (N-acetylneuraminic acid), respectively. Iso-electric focusing separates normal transferrin with high resolution into isoforms depending on iron saturation, content of sialic acid (SA) or amino acid substitutions. After complete iron saturation (2 Fe atoms per molecule) transferrin normally separates into 4 isoforms named after their approximate isolectric point (pI) pI 5.2 (5 SA), pI 5.4 (4 SA, major fraction), pI 5.6 (3 SA) and pI 5.7 (2 SA). Small amounts of transferrin with pI 5.6 and 5.7 are present in normal serum. The isoform which markedly increases in serum from alcoholics is pI 5.7. The pI 5.7 fraction is normally less than 0.8% of total transferrin, but may be increased more than tenfold after heavy alcohol consumption. After excessive drinking an additional pI 5.9 fraction (0 SA) may appear. The pI 5.7 and pI 5.9 fractions represent carbohydrate deficient transferrin (CDT).

The purpose of this invention is to develop an HPLC (high performance liquid chromatography) method suitable for routine use in laboratories to identify subjects at high risk for alcohol dependence and to evaluate its sensitivity and specificity for detecting heavy alcohol consumption in defined populations. The object is to present a method suitable for clinical standard procedures that specifically measures the concentration of CDT, which is a suitable biochemical marker for heavy alcohol consumption during the preceding weeks.

SUMMARY OF THE INVENTION

The present invention is for a method of separating and quantitating CD-transferrin in blood serum. The blood serum is saturated with iron to produce isoforms of transferrin, which is then separated from other serum proteins. A chromatogram of the isoforms of transferrin is then developed to relate the separated isoforms with different pI values. The separation is preferably carried out in an ion exchange column using a salt gradient. The chromatogram is preferably developed using a high performance liquid chromatograph (HPLC).

BRIEF DESCRIPTION OF THE FIGURES

The method of the invention is described in greater detail below by means of some Figures, in which:

FIG. 3 shows, in tabular form, the salt gradient used when separating transferrin isoforms.

DETAILED DESCRIPTION OF THE INVENTION

Samples were prepared in that fresh serum or serum frozen at −20° C. for less than 6 months was saturated with iron by addition of 25 µl of NaHCO$_3$ (500 mmol/l and 18 µl FeCl$_3$ (10 mmol/l) per ml of serum. After mixing and storage at +8° C. overnight, the lipoproteins were precipitated by adding 10 µl of Dextranesulfate (10% (w/v)) and 50 µl of CaCl$_2$ (1 mol/l) per ml serum. This mixture was stored for 30–60 min. at +8° C. and then centrifuged at 10 000 ×g for 10 min. The supernatant was diluted fivefold with water and transferred to an HPLC autoinjector.

The transferrin isoforms were separated on an ion exchange column, Mono Q®HR 5/5 (Pharmacia Biotechnology, Sweden) from other serum proteins by a salt gradient for 32 min. including regeneration. Starting buffer (A) was Bis Tris 20 mmol/l pH 6.2. Buffer B was buffer A plus NaCl 350 mmol/l at the same pH. Solution C, NaCl 1 mol/l, was used for regeneration. Before use all solutions were degassed and filtered through a 0.45 µm pore—size filter. Samples of 200 µm were injected, the flow rate was maintained at 1 ml/min. providing the gradient profile shown in the table of FIG. 3.

The HPLC system used consisted of pump No. 2941 (Pharmacia Biotechnology, Sweden), a Jasco 870 UV detector equipped with a 460 nm filter and a 10 mm flow cell together with a tungsten lamp. The system contained an autoinjector, Waters WISP 715, with a cooling system for 96 samples. An Schimazu CR 5A integrator was used for calculating the peak areas according to the valley-valley mode.

Figure 1:
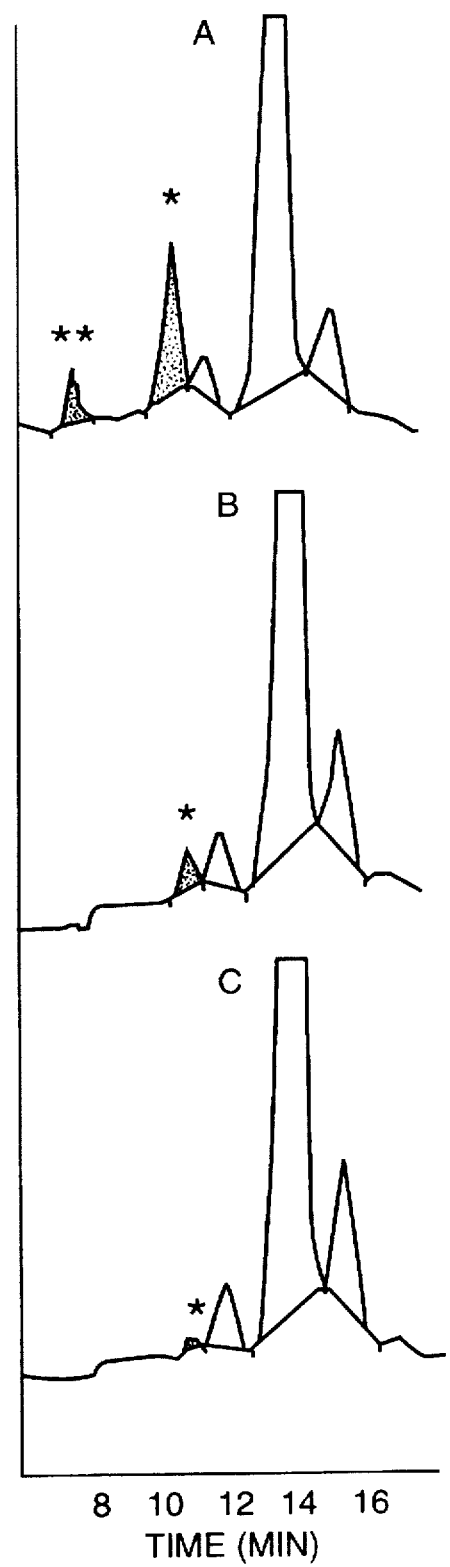
FIGS. 1A, 1B, and 1C show chromatograms for transferrin isoforms from samples from individuals with varying alcohol consumption.

Transferrin isoforms have pI:s between approximately 5.2 –5.9. Optimal separation of the most cathodal isoforms was obtained at pH 6.2. Nevertheless, acceptable results have been obtained also with buffer solutions having pH values between 6.0 and 6.4. However, for the best result pH should be between 6.1 and 6.3, and most preferably pH should be 6.2. The addition of NaHCO$_3$ together with FeCl$_3$ gives an optimal stable iron saturation. Precipitation of lipoproteins improves the separation of the pI 5.9 isoform which can be hidden under heavy β-lipoprotein fractions in some patients. Fasted samples with lower levels of lipoprotein cannot be used in working with alcoholics on ambulatory bases. FIG. 1 illustrates chromatograms after HPLC from heavily, medium and normal drinking individuals, where the pI 5.9 isoform also appears in the first pattern. The absorbance of the Fe-transferrin complex at 460 nm is approximately 1/10 of the 280 nm absorbance, but is highly specific for the transferrin fractions. The amount of CD-transferrin, pI 5.7 represents only 0.2–0.8% (mean ±2 S.D.) of the total transferrin in teetotallers and occasional drinkers. This value was slightly dependent on the method of integration of the chromatography profile. Slightly higher values were found using baseline integration, but the valley-valley method was more reproducible.

In FIG. 1, A represents a sample from an individual with the consumption of 300 g alcohol/24 h, B represents a sample from an individual having consumed 70 g alcohol/24 h, and C indicates a normal pattern.

The shadowed areas show CDT, i.e. transferrin isoforms having pI 5.7 (*) and pI 5.9 (**). The other peaks of the chromatograms represent, from the right, pI 5.2, 5.4 and 5.6, respectively. It is obvious from the chromatograms that the dominating fraction is pI 5.4. It is further obvious that the values of CDT are increased after heavy alcohol consumption. The absorbance of the Fe-transferrin complex was measured at 460 nm.

Figure 2:
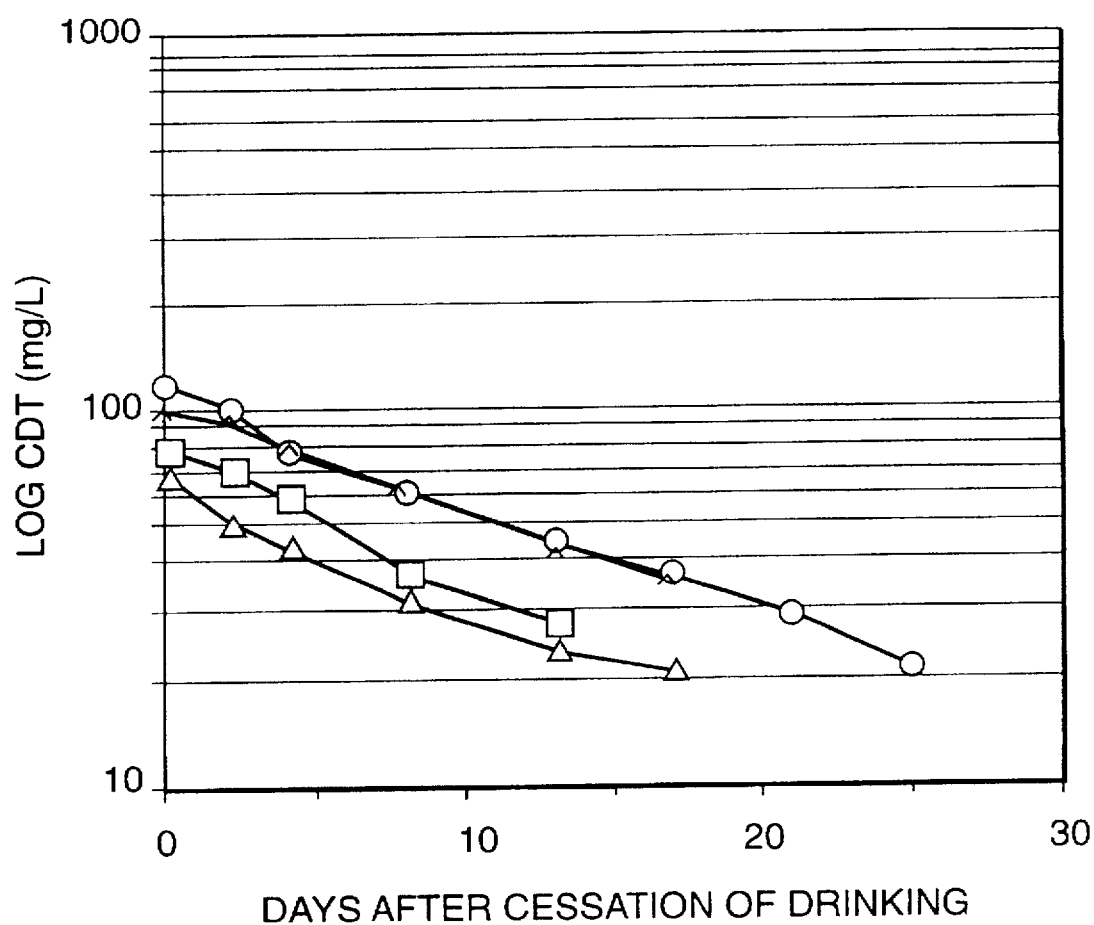
FIG. 2 shows how the concentration of CDT decreases after drinking for four heavily intoxicated patients.

The half-life of CD-transferrin was studied by measuring the CDT pI 5.7 of four heavily intoxicated patients sequentially for 15 days hospitalisation at which time no relapse of alcohol abuse occurred. The total transferrin concentration was measured in each sample (g/l) and CDT was calculated and given as mg/l in a semilogarithmic diagram (FIG. 2). Total transferrin concentration increased with time in some patients during the hospitalisation. The half-life of each curve was read from its linear slope. There was a difference between individual patients and the mean T½ was estimated to be 9.5±1 days.

Figure 4:
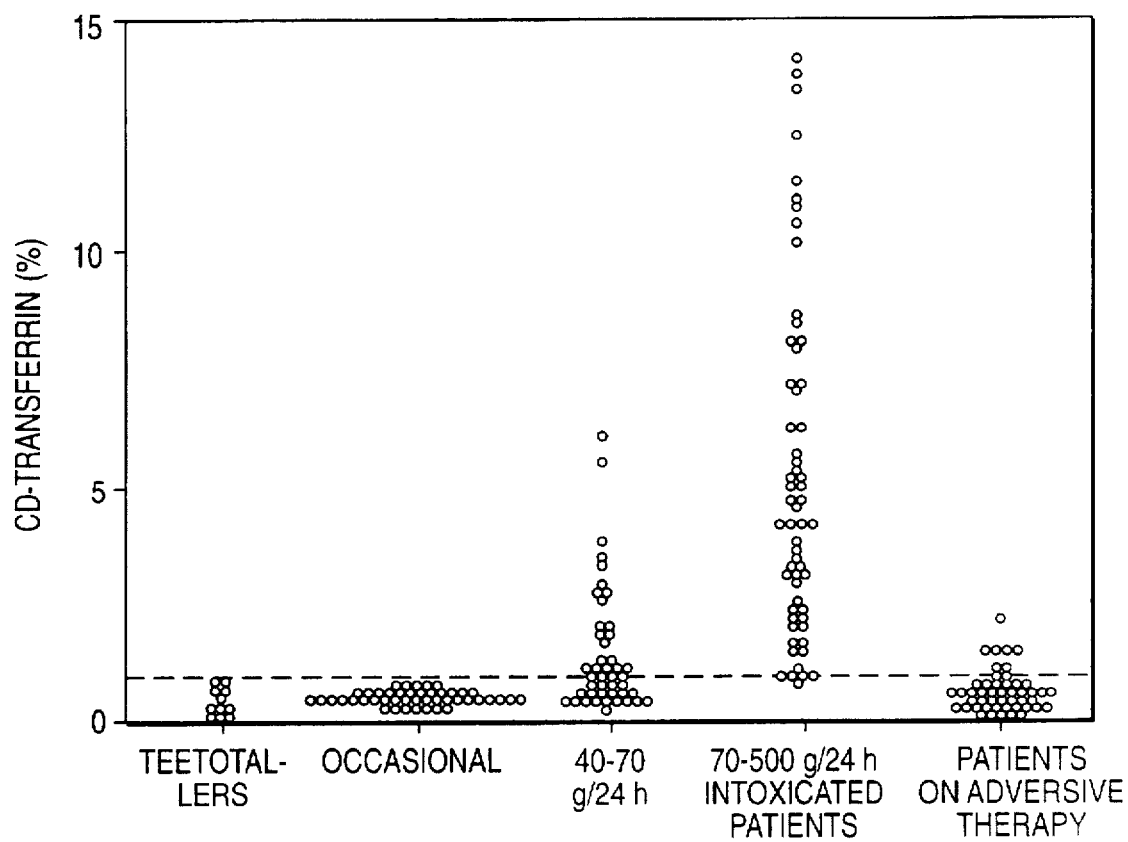
FIG. 4 shows CDT levels in sera of individuals with different alcohol consumption.

CDT values found in samples from teetotallers and occasional drinkers (laboratory staff) showed a normal distribution and were consistently below 1%. using valley-valley integration (FIG. 4). Among 284 men from the general city population with a previous record of high γ-GT values 20%. declared an alcohol consumption of 40–70 g/24 h. In these men the sensitivity of CDT was 55% and the specificity 91% using the cut off level of 0.8%. Among the heavily intoxicated drinkers (70–500 g/24 h) the sensitivity was nearly 100%. Normalisation of CDT was seen in 84% during aversion therapy. Some of them have not yet reached their basal CDT level. We cannot exclude moderate drinking during treatment with calcium carbide tablets.

The method gives reproducible results and can be automated for large sample series. Forty patient samples can be analyzed during 24 hours. The costs for reagents including investments for HPLC are approximately 30% of the reagent costs for the disposable minicolumns combined with radioimmunoassay (Pharmacia Diagnostics). This technique has to be run in duplicates. Another advantage of HPLC is the visible document of the specific 460 nm absorbance which is of importance in the genetic variation of transferrin. Serum from alcoholics are often lipemic and some lipoproteins as well as other serum proteins may precipitate at pH 6.2 causing a gradual increase in column pressure. It is therefore convenient to use two columns so analyses can be performed during regeneration of one column. This approach has provided us with one year of experience (>1000 samples) with no problems. Genetic variants of transferrin are estimated to be present in about 29% of the population. Most of them represent subtypes of the major TfC phenotype with minor changes in pI:s. They do not interfere with the chromatography pattern. Only TfBC heterozygotes and TfCD heterozygotes, frequency 1–2/o o in Caucasian population will interfere with the chromatography profile. In these cases it is necessary to confirm the results with isoelectric focusing in a specialized laboratory.

To confirm the method of the invention albumin was removed from serum by pretreatment with Blue-Sepharose®. Disposable columns (polypropylene 5 ml, Pierce) were packed with swollen Blue-Sepharose® Cl-6B (Pharmacia Biotechnology, Sweden) corresponding to 0.2 g (dry weight). After rinsing according to the manufacture's instruction the small column was equilibrated with glycin, 100 mmol/l, pH 7.2. 100 µl of the ironsaturated and lipoprotein free supernatant was mixed with 2 µl β-mercaptoethanol 10% (v/v) and after one hour at room temperature applied to the mini-column. Serum proteins were eluted with glycin, 100 mmol/l, pH 7.2.

The first 300 µl of the eluate was discarded, 40 µl of the next mixed 800 µl was used for isoelectric focusing. Each column can be used several times after regneration with urea 6 mol/l followed by glycin 0.1 mol/l, pH 7.0.

Isoelectric focusing was performed essentially as described for $α_1$-antitrypsin with the following modifications. The ampholyte mixture was equal parts of Pharmalyte® 4–6.5 and Pharmalyte®5–6, total 1.9 ml per 30 ml gel solution. The same procedure can be performed on a smaller scale using the Phast System (Pharmacia Biotechnology, Sweden). Transferrin isoforms can be verified by immunofixation using cellulose acetate membranes impregnated with transferrin antibodies. All pathological results from HPLC (CDT>0.8%) have so far been confirmed by isoelectric focusing.

The serum transferrin concentration was estimated by electroimmunoassay using antisera from Dako (Denmark).

Our procedure gives automatically the calculated percentage of CDT from the integrator and eliminates the need for specific determination of transferrin concentration. The observation of large variation of total transferrin concentration in women with increases due to iron deficiency and estrogen administration and highly intoxicated alcoholics (range 1.1–3.6 g/l) in this work motivates the use of percentage CDT of total amount transferrin rather than absolute quantities. The half-life of approximately 9.5 days for the pI 5.7 isoform allows evaluation of alcohol consumption during the past 1–3 weeks or verifies a successful treatment. This result is in agreement with the published half-life of 8–10 days for normal transferrin rather than the recently estimated 15 days for CDT.

When CDT is elevated it is a very specific marker for alcohol abuse and greatly superior to other currently available biological markers. In an evaluated population of middle-aged males the individuals have been very thoroughly characterized and followed over 15 years. At a follow-up in 1991 the alcohol consumption was assessed by two trained nurses and blood sampled for CDT at the same occasion. We found a sensitivity of 55% in the group that reported an alcohol consumption of more than 40 g/day. However, in the study of intoxicated individuals consuming more than 70 g/day the sensitivity was near 100%. The high specificity in the teetotallers and the occasional drinkers, near 100% allows the conclusion that CDT has the highest specificity of the available biological markers.

What is claimed is:

1. A method for separating and quantitating isoforms of carbohydrate deficient transferrin (CDT) in blood serum comprising:
   (a) saturating a blood serum sample with iron to provide isoforms of Fe-transferrin complexes in the blood serum sample;
   (b) separating the isoforms of Fe-transferrin complexes from other serum proteins in the blood serum sample with an ion exchange column using a salt gradient; and
   (c) developing a chromatogram using a high performance liquid chromatograph (HPLC) and by measuring absorbance at 460 nm of the isoforms of Fe-transferrin complexes, which chromatogram relates the separated isoforms of Fe-transferrin complexes with different pI values.

2. The method of claim 1 in which the separation takes place in a buffer solution having a pH of between 6.0 and 6.4.

3. The method of claim 2 in which the pH is between 6.1 and 6.3.

4. The method of claim 3 in which the pH is 6.2.

5. The method of claim 1 which further comprises calculating the CDT elevation.

6. The method of claim 1 in which the saturation step is carried out by adding solutions of sodium bicarbonate and ferric chloride to the blood serum sample.

7. The method of claim 6 which includes the addition of 25 µl of a 500 mmol/l solution of sodium bicarbonate and 18 µl of a 10 mmol/l solution of ferric chloride per ml of serum.

8. The method of claim 6 which further comprises precipitating lipid proteins present in the blood serum sample.

9. The method of claim 8 which includes adding solutions of dextranesulfate and calcium chloride to the blood serum sample, mixing the resulting mixture and storing same.

10. The method of claim 9 in which the mixture is stored for 30–60 minutes at +8° C. and then centrifuged.

11. The method of claim 10 which further comprises diluting the supernatant obtained from the centrifugation step.

12. The method of claim 11 in which the supernatant is diluted five-fold with water.

13. The method of claim 12 which further comprises injecting the diluted supernatant into an HPLC.

14. The method of claim 6 in which the resulting mixture is stored overnight.

15. The method of claim 1 which further comprises integrating peaks of the chromatogram.

16. The method of claim 1 which further comprises associating peaks of the chromatogram with heavy alcohol consumption.

* * * * *